(12) United States Patent
Vercruysse

(10) Patent No.: US 9,261,648 B2
(45) Date of Patent: Feb. 16, 2016

(54) PLASMONIC WAVELENGTH SELECTIVE SWITCH

(71) Applicants: IMEC VZW, Leuven (BE); Katholieke Universiteit Leuven, KU LEUVEN R&D, Leuven (BE)

(72) Inventor: Dries Vercruysse, Sint Andries (BE)

(73) Assignees: IMEC VZW, Leuven (BE); Katholieke Universiteit Leuven, KU LEUVEN R&D, Leuven (BE)

( * ) Notice: Subject to any disclaimer, the term of this patent is extended or adjusted under 35 U.S.C. 154(b) by 0 days.

(21) Appl. No.: 14/570,608

(22) Filed: Dec. 15, 2014

(65) Prior Publication Data

US 2015/0168648 A1    Jun. 18, 2015

(30) Foreign Application Priority Data

Dec. 14, 2013    (EP) .................................... 13197308

(51) Int. Cl.
| | |
|---|---|
| *G01N 21/64* | (2006.01) |
| *G02B 6/122* | (2006.01) |
| *G02B 6/12* | (2006.01) |
| *B82Y 10/00* | (2011.01) |
| *G02B 5/00* | (2006.01) |
| *B82Y 20/00* | (2011.01) |

(52) U.S. Cl.
CPC .............. *G02B 6/1226* (2013.01); *B82Y 10/00* (2013.01); *G01N 21/648* (2013.01); *G01N 21/6428* (2013.01); *G02B 5/008* (2013.01); *G02B 6/12007* (2013.01); *B82Y 20/00* (2013.01); *G01N 2021/6441* (2013.01); *G01N 2201/068* (2013.01); *G02B 2006/12138* (2013.01); *G02B 2006/12145* (2013.01); *G02B 2207/101* (2013.01); *Y10S 977/95* (2013.01); *Y10S 977/954* (2013.01)

(58) Field of Classification Search
CPC .. G02B 6/1226; G02B 6/12007; G02B 6/122; G01N 21/648; G01N 21/553
See application file for complete search history.

(56) References Cited

U.S. PATENT DOCUMENTS

| | | | |
|---|---|---|---|
| 8,503,075 B2 * | 8/2013 | Consonni et al. ............. | 359/360 |
| 2012/0235067 A1 * | 9/2012 | Araci et al. ............... | 250/504 R |

OTHER PUBLICATIONS

European Search Report, European Patent Application No. 13197308, dated Mar. 13, 2014.

(Continued)

*Primary Examiner* — Marcus Taningco
(74) *Attorney, Agent, or Firm* — McDonnell Boehnen Hulbert & Berghoff LLP

(57) ABSTRACT

A plasmonic structure comprises a substrate and an electro conductor provided in or on the substrate. The electro conductor comprises a first part configured to provide a first series of plasmon resonance modes (for incident radiation of a first wavelength) and a second part configured to provide a second series of plasmon resonance modes (for incident radiation of a second wavelength). The first and second parts are functionally connected in a linkage region, wherein the electro conductor is shaped such as to form a capacitive gap. The electro conductor is further configured to direct radiation incident on the plasmonic structure of the first wavelength predominantly toward a first direction and to direct radiation incident on the plasmonic structure of the second wavelength predominantly toward a second direction, in which the first direction and the second direction are separated by an angle of at least 60°.

15 Claims, 11 Drawing Sheets

(56) References Cited

OTHER PUBLICATIONS

Shegai, Timur et al., A Bimetallic Nanoantenna for Directional Colour Routing, Nature Communications, vol. 2, No. 481, Sep. 20, 2011, pp. 1-6.

Lavasani, S.H. Alavi et al., "Color-Switched Directional Ultracompact Optical Nanoantennas", Journal of the Optical Society of America B, vol. 29, No. 6, Jun. 2012, pp. 1361-1366.

Jie, Yao et al., "An Antenna to Direct Light to Opposite Directions", Optics Communications, vol. 300, Mar. 20, 2013, pp. 274-276.

* cited by examiner

PLASMONIC WAVELENGTH SELECTIVE SWITCH

CROSS-REFERENCE TO RELATED APPLICATION

This application claims priority to European Patent Application No. 13197308.3 filed on Dec. 14, 2013, the contents of which are hereby incorporated by reference.

FIELD OF THE DISCLOSURE

The disclosure relates to the field of surface plasmon resonance photonics. More specifically it relates to a plasmonic wavelength selective switch.

BACKGROUND OF THE DISCLOSURE

It is known in the art that surface plasmon resonance in nano scale structures, such as nanoparticles, can be used for directing electromagnetic radiation in the visible spectrum in a manner similar to the directional transmission by radiofrequency antennas. For example, in the radiofrequency spectrum, a typical antenna design for high directivity is the Yagi-Uda antenna, which comprises a linear array of antenna elements, where an array of nanoparticles can provide a similar radiation pattern in the optical regime. Directional control of visible spectrum radiation can thus be obtained by a nano-optical Yagi-Uda antenna comprising, for example, an appropriately configured arrangement of gold nano rods.

Plasmonic antennas may be useful components for microscopic or nano scale optical systems. For example, sending or receiving photons in a directionally selective fashion may find application in the field of micro- and nano scale photonics. By such directional sending or receiving of photons, signals may be transmitted in a well-defined direction or the signal to noise ratio of a detector may be increased by such directionally selective components. Furthermore, wavelength dependent directivity may be particularly advantageous for scaling sensors. Plasmonic sensors are usually based on detecting changes in the spectrum of radiation coming from an object of interest, e.g. scattered, transmitted or fluorescent radiation. Spectral information is typically recovered by gratings or filters. These components are large compared to plasmonic antennas, and furthermore are hard to miniaturize. If the spectral information would already be present in the scatter or emission patterns coming from the antenna this can simplify spectral analysis, and thus may result in cheaper, more compact devices.

The split ring resonator has been studied in the art as an artificial magnetic atom. It has also been shown, for example by Yao Jie et al. in "An Antenna to Direct Radiation to Opposite Directions," Optics Communications 300, p. 274-276, that a split ring resonator can be used as an optical antenna to direct radiation emitted by an electric source to different directions at different wavelengths. This phenomenon, according to Jie et al., can be explained by a two-dipole model.

SUMMARY OF THE DISCLOSURE

It is an object of embodiments of the present disclosure to provide simple and efficient means and methods for selective switching different wavelengths of radiation into different spatial directions.

It is an advantage of embodiments of the present disclosure that optical signals may be switched as a function of their wavelength in a well-defined direction corresponding to that wavelength.

It is an advantage of embodiments of the present disclosure that the signal to noise ratio of a detector may be increased by using a directionally selective component according to embodiments. It is a further advantage that small-scale nanophotonic integration can be achieved by embodiments of the present disclosure.

It is an advantage of the present disclosure that the use of components according to the present disclosure in a nanophotonic device can lead to a cheap and compact device.

It is an advantage of embodiments of the present disclosure that a functional structure for selective wavelength switching is provided that only requires a few components, e.g. a single simple structure, and few different materials, e.g. a single electro conductor material provided in or on a single substrate material.

It is an advantage of embodiments of the present disclosure that radiation of different wavelengths can be directed in more than one distinct wave-length specific direction.

It is an advantage of embodiments of the present disclosure that directionality and wavelength dependence of a structure according to embodiments can be easily tuned.

It is an advantage of embodiments of the present disclosure that a plasmonic structure is provided which shows good interaction properties with quantum emitters.

The above objective is accomplished by a method and device according to the present disclosure.

The present disclosure relates to a plasmonic structure comprising a substrate and at least one electro conductor provided in or on the substrate. The at least one electro conductor comprises a first part configured to provide a first series of plasmon resonance modes for incident radiation—the incident radiation may result in directive radiation at a first wavelength—and a second part configured to provide a second series of plasmon resonance modes for incident radiation—the second part may result in directive radiation at a second wavelength. The first part and second part are functionally connected in a linkage region, and the electro conductor is shaped in the linkage region such as to form a capacitive gap. The electro conductor is further configured to direct radiation incident on the plasmonic structure of the first wavelength predominantly toward a first direction and to direct radiation incident on the plasmonic structure of the second wavelength predominantly toward a second direction. In one example, the first direction and the second direction are separated by an angle of at least 60°. It is an advantage of embodiments of the present disclosure to provide a plasmonic structure wherein dependent on the wavelength, incident radiation or fluorescent radiation that is created is guided into different directions.

The first direction and the second direction may be substantially opposite spatial directions. It is an advantage of embodiments of the present disclosure that the radiation is emitted/scattered in distinct directions. It is an advantage of embodiments of the present disclosure that such directivity allows accurate and easier manufacturing, e.g. waveguides can more easily be defined in the structure.

The first part may form a first plasmonic split ring resonator and the second part may form a second plasmonic split ring resonator. It is an advantage of embodiments of the present disclosure that efficient emission or scattering of radiation in distinct directions is obtained.

The first plasmonic split ring resonator and the second plasmonic split ring resonator may each have an elliptical shape. In another example, the first plasmonic split ring resonator and the second plasmonic split ring resonator may have a block-like shape.

The electro conductor may comprise a noble metal. It may comprise aluminum.

The substrate may comprise glass.

The substrate may form part of a waveguide in an integrated photonics system.

The capacitive gap may comprise a quantum emitter or the capacitive gap may be functionalized to capture a quantum emitter.

The present disclosure also relates to a sensor comprising a plasmonic structure as described herein, a first radiation detection element and a second radiation detection element. The plasmonic structure may be arranged such as to direct radiation incident on the plasmonic structure of the first wavelength predominantly toward the first radiation detection element, and to direct radiation incident on the plasmonic structure of the second wavelength predominantly toward the second radiation detection element. It is an advantage of embodiments of the present disclosure that a sensor can be obtained wherein the use of a grating for spectrally splitting incident or induced radiation can be avoided. It is an advantage of embodiments of the present disclosure that spectrally splitting radiation can be obtained using components with a small footprint, thus allowing miniaturization of the system.

The sensor further may comprise a filter covering the first radiation detection element and the second radiation detection element, the filter being adapted for filtering out the portion of a radiation wave incident on the plasmonic structure that is transmitted through the plasmonic structure substantially unaffected.

The sensor may comprise a sample positioning means for bringing a sample into contact with the plasmonic structure. It is an advantage of embodiments according to the present disclosure that a sensor is provided for characterizing a sample. Such a sample may be a fluid although embodiments of the present disclosure are not limited thereto.

The sensor may comprise an excitation source for exciting fluorescent labels being positioned near the plasmonic structure, the sensor furthermore being adapted for characterizing differently fluorescent labeled targets of interest in the sample. The sensor thus may help to detect different targets of interest in the sample. The sample may be provided using a microfluidic channel.

The sensor may comprise a processor for processing radiation sensed at the first and/or second radiation detection element and/or for determining a ratio of the amount of radiation detected in the first radiation detection element and the amount of radiation detected in the second radiation detection element. It is an advantage of embodiments according to the present disclosure that the ratio of the amounts of radiation detected in the different radiation detection elements can be used as a discriminator to identify changes in the incident or induced radiation and thus in a sample to be characterized and brought into contact with the plasmonic structure.

The present disclosure relates to a method for wavelength selective switching of radiation, the method includes providing a plasmonic structure comprising an electro conductor which includes a first part configured to provide a first plasmon resonance mode for incident radiation of a first wavelength and a second part configured to provide a second plasmon resonance mode for incident radiation of a second wavelength. The first part and second part are functionally connected in a linkage region. The electro conductor is further configured to direct radiation incident on the plasmonic structure of the first wavelength predominantly toward a first direction and to direct radiation incident on the plasmonic structure of the second wavelength predominantly toward a second direction. The method also includes impinging a radiation wave onto the plasmonic structure such as to direct a first component of the radiation wave corresponding to the first wavelength toward the first direction and to direct a second component of the radiation wave corresponding to the second wavelength toward the second direction.

The method further may comprise introducing a fluorophore in or near a capacitive gap formed in the linkage region, determining a radiative property of the first component of the radiation wave and of the second component of the radiation wave, and determining a property of the fluorophore taking into account the determined radiative property of the first component and the second component.

The method may comprise evaluating a ratio of the radiation directed to the first direction and the radiation directed to the second direction.

Particular and preferred aspects of the disclosure are set out in the accompanying independent and dependent claims. Features from the dependent claims may be combined with features of the independent claims and with features of other dependent claims as appropriate and not merely as explicitly set out in the claims.

These and other aspects of the disclosure will be apparent from and elucidated with reference to the embodiment(s) described hereinafter.

Figure 1:
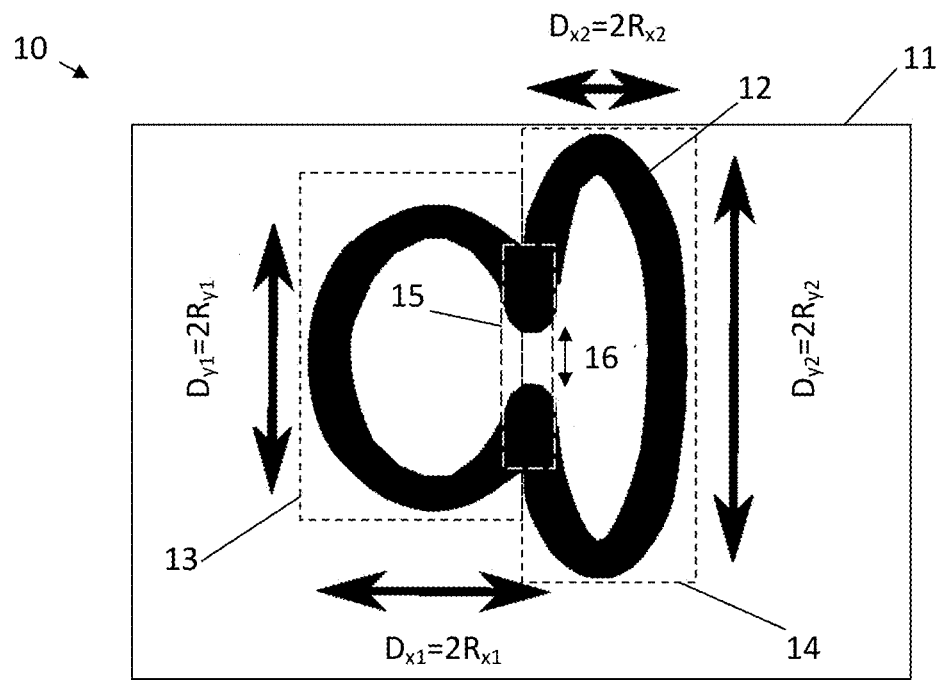
FIG. 1 shows a plasmonic structure according to embodiments of the present disclosure.

The drawings are only schematic and are non-limiting. In the drawings, the size of some of the elements may be exaggerated and not drawn on scale for illustrative purposes.

In the different drawings, the same reference signs refer to the same or analogous elements.

DETAILED DESCRIPTION OF ILLUSTRATIVE EMBODIMENTS

The present disclosure will be described with respect to particular embodiments and with reference to certain drawings but the disclosure is not limited thereto but only by the claims. The drawings described are only schematic and are non-limiting. In the drawings, the size of some of the elements may be exaggerated and not drawn on scale for illustrative purposes. The dimensions and the relative dimensions may not correspond to actual reductions to practice of the disclosure.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the disclosure described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present disclosure, the only relevant components of the device are A and B.

Reference throughout this specification to "one embodiment" or "an embodiment" means that a particular feature, structure or characteristic described in connection with the embodiment is included in at least one embodiment of the present disclosure. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of example embodiments of the disclosure, various features of the disclosure are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed disclosure requires more features than are expressly recited in each claim. Rather, as the following claims reflect, inventive aspects may lie in less than all features of a single foregoing disclosed embodiment. Thus, the claims following the detailed description are hereby expressly incorporated into this detailed description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

In a first aspect, the present disclosure relates to a plasmonic structure which comprises an electro conductor provided in or on a substrate. The electro conductor comprises a first part configured to provide a first series of plasmon resonance modes (for incident radiation which result in directive radiation for a first wavelength) and the electro conductor also comprises a second part configured to provide a second series of plasmon resonance modes (for incident radiation which result in directive radiation for a second wavelength). The first part and the second part are furthermore functionally connected in a linkage region. In this linkage region, the electro conductor is shaped such as to form a capacitive gap. The electro conductor is furthermore configured to direct radiation incident on the plasmonic structure of a first wavelength predominantly toward a first direction and to direct radiation incident on the plasmonic structure of a second wavelength predominantly toward a second direction, in which this first direction and this second direction are separated by an angle of at least 60°, for example in which the first direction and the second direction are substantially opposite spatial directions, e.g. are opposite spatial directions.

Standard and optional features will further be described with reference to FIG. 1, which illustrates an example of a structure according to the present disclosure, although embodiments are not limited thereto.

Referring to FIG. 1, a plasmonic structure 10 according to embodiments of the present disclosure is shown. The plasmonic structure 10 may comprise a substrate 11, e.g. an optical substrate such as a silicon, silicon nitride or silicon dioxide substrate, e.g. a silicon-on-insulator substrate. The substrate 11 may for example comprise glass, e.g. the substrate may be a glass substrate.

However, in embodiments according to the present disclosure, the substrate 11 may form part of a waveguide in an integrated photonics system. It is an advantage of such embodiments that the plasmonic structure 10 can be sufficiently small to be, for example, integrated in the top cladding of a waveguide structure. The plasmonic structure 10 may advantageously direct radiation of the first wavelength towards one direction of the waveguide, and radiation of the second wavelength towards the other direction of the waveguide, thus avoiding or complementing conventional spectral switching means, such as diffractive gratings.

The plasmonic structure 10 comprises an electro conductor 12 provided in or on the substrate 11. Such electro conductor 12 may comprise an electrically conducting medium suitable for surface plasmon resonance structures, for example a metallic material such as a noble metal, e.g. gold or silver, or aluminium. For example, the electro conductor 12 may be a semi-transparent noble metal provided on the substrate in a patterned coating. Such electro conductor 12 may be provided onto the substrate under conditions of total internal reflection, e.g. such that a condition of total internal reflection exists at the interface. The thickness of the noble metal layer, e.g. gold, that can be used may in one example be about 50 nm. Typically the thickness of these kinds of structures can vary between 20 nm and 100 nm. In one example, the width may be between 40 nm and 60 nm, depending on the thickness of the end material that can be reached. Typically, the width of the structure may vary between 20 nm and 200 nm.

The electro conductor 12 comprises a first part 13 configured to provide a first series of plasmon resonance modes for incident radiation (which result in directive radiation at a first wavelength). Furthermore, the electro conductor comprises a second part 14 configured to provide a second series of plasmon resonance modes for incident radiation (which causes directive radiation at a second wavelength). Particularly, the plasmon resonance modes associated with the first part and the plasmon resonance modes associated with the second part may have peak resonance wavelengths which are clearly distinct, e.g. which leads to separation of the first and second wavelengths by at least 50 nm, e.g. by at least 100 nm.

The first part 13 may form a first plasmonic split ring resonator and the second part may form a second plasmonic split ring resonator, e.g. the first part 13 and the second part 14 each in isolation have the shape and configuration of a plasmonic split ring resonator, e.g. as known to the person skilled in the art. Although the first plasmonic split ring resonator and/or the second split ring resonator may have any shape as known for surface plasmon split ring resonators in the art, e.g. rectangular or circular, in one embodiment, the first plasmonic split ring resonator and the second plasmonic split ring resonator may each have an elliptical shape. However, in other embodiments, the first plasmonic split ring resonator and the second plasmonic split ring resonator may differ in shape and/or dimensions, such as to provide a substantial difference in the peak resonance wavelengths of the first plasmon resonance modes and the second plasmon resonance modes.

In order to provide some insights in how a plasmonic split ring resonator operates, some further description is provided below.

Figure 2:
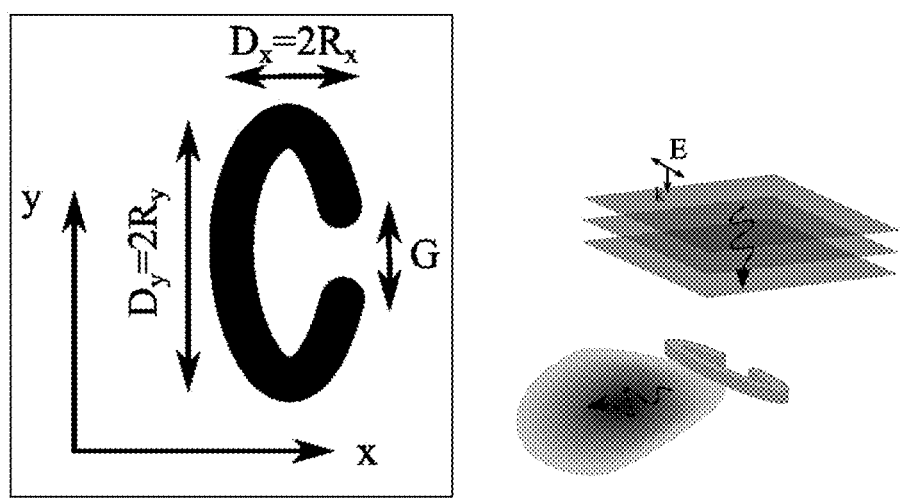
FIG. 2 shows an example single split ring resonator as known in the art, and a schematic representation of directional scattering of an incident planar wave by such resonator.
Figure 3:
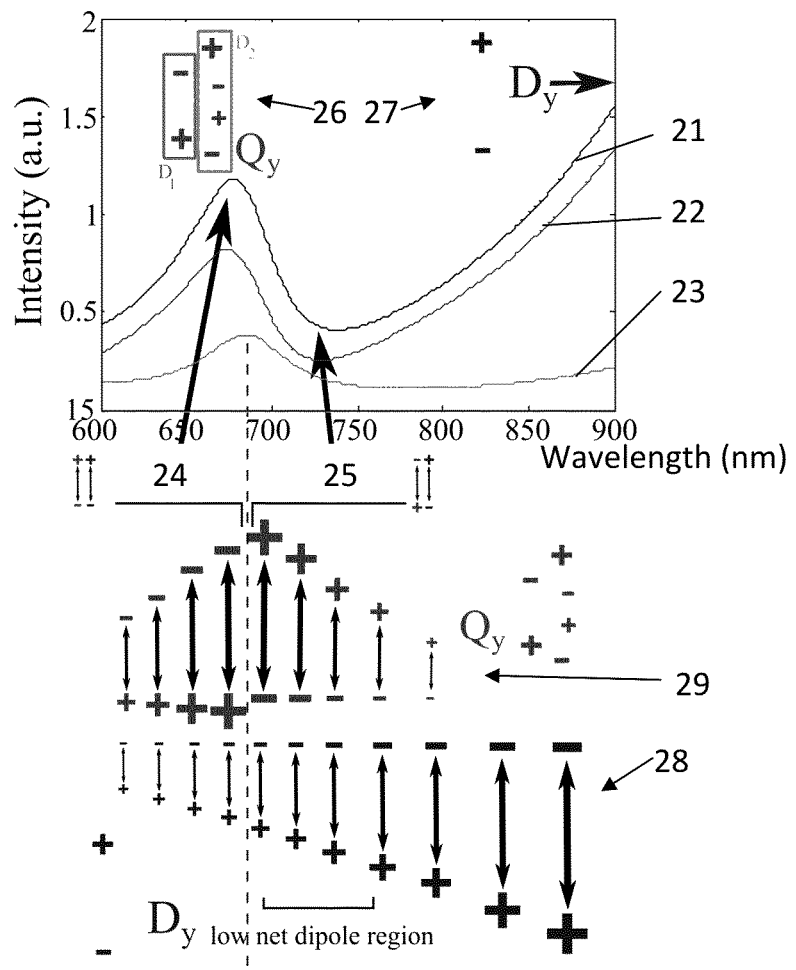
FIG. 3 shows the extinction, scattering and absorption spectrum of a single split ring resonator, as known in the art, and a schematic representation of the Fano interference in such single split ring resonator.

In FIG. 2 such a plasmonic split ring resonator, e.g. forming the first part 13 or second part 14 in a structure according to embodiments, is shown in isolation. Directionality in one direction can be obtained by a single split ring resonator, as illustrated by the schematic representation of the scattering of an incident planar electromagnetic wave E having wave vector k in FIG. 2. The ring may be generally elliptical in shape with a capacitive gap defined in the ring. Such ring can be defined by a radius along the x-axis, $R_x$, a radius along the y-axis, $R_y$, and a width, G, of the capacitive gap provided between the open ends of the split ring. The extinction 21, scattering 22 and absorption 23 spectrum of such an example resonator for y-polarized radiation between 600 nm and 900 nm is shown in FIG. 3. At 690 nm, the quadrupole resonance, $Q_y$, can be seen. It lies in the tail of a dipole resonance, $D_y$, which has a wavelength above 900 nm. A schematic representation of the charge of these plasmonic modes can be seen in the insets 26 and 27 of FIG. 3. Since both the resonances are Y-polarized, they can be excited by the same incoming radiation beam and will interfere. This type of interference is known as a Fano interference and can be recognized in the spectra by an asymmetric resonance scattering peak. In the case of this example split ring resonator, increased scattering is observed below the resonance wavelength and reduced scattering is seen above the resonance wavelength. This asymmetry can be explained by constructive interference 24 and destructive interference 25 between $Q_y$ and $D_y$ on respective sides of the peak. Below the spectral graph in FIG. 3, the net dipole contributions of the two modes are schematically depicted along the spectra. For the $D_y$-resonance 28, the intensity decreases with decreasing wavelength and the phase relative to the incoming beam is relatively constant. The net dipole contribution of the $Q_y$ resonance 29 is largest around the resonance wavelength. In addition there is a phase change at the resonance wavelength. Thus the asymmetry may be explained. On the left side both the resonances are in phase and they interfere constructively, causing a large dipole and increased scattering. On the right side, the resonances are out of phase and so they interfere destructively, causing a small dipole and decreased scattering.

Figure 4:
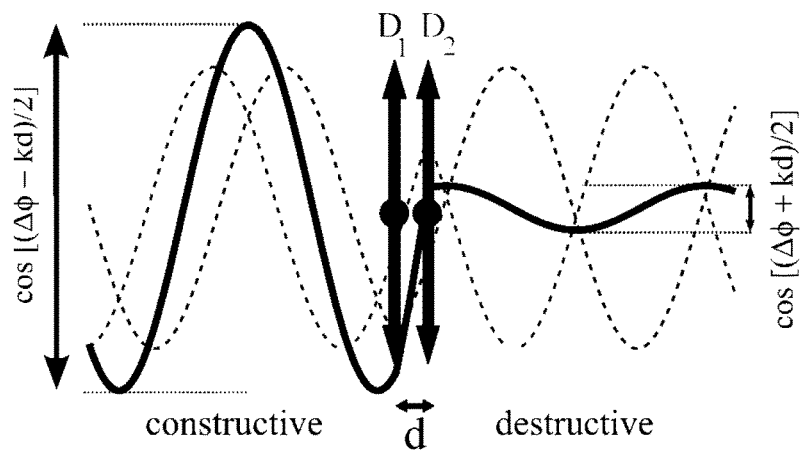
FIG. 4 illustrates the directional scattering by asymmetric constructive interference and destructive interference of two dipoles with a phase difference, $\Delta\phi$, separated by a distance, d, in a single split ring resonator, as known in the art.

In the spectral region on the right side of the $Q_y$ resonance, where the net dipole is small to non-existing, scattering is the result of the phase difference of the different dipoles as indicated in the $Q_y$ inset 26. Radiation in a certain direction in this case is dependent on the phase difference, $\Delta\phi$, and the spatial distance, d, between the dipoles seen in this direction. When the phase difference matches the spatial distance, the radiation in a direction can be eliminated by destructive interference in one direction while being quite large, due to constructive interference, in the opposite direction. In other words at the right side of the resonance, thus the red side of the spectrum, the absence of a net dipole can lead to high directionality if d and $\Delta\phi$ match. This effect is depicted in FIG. 4.

Figure 5:
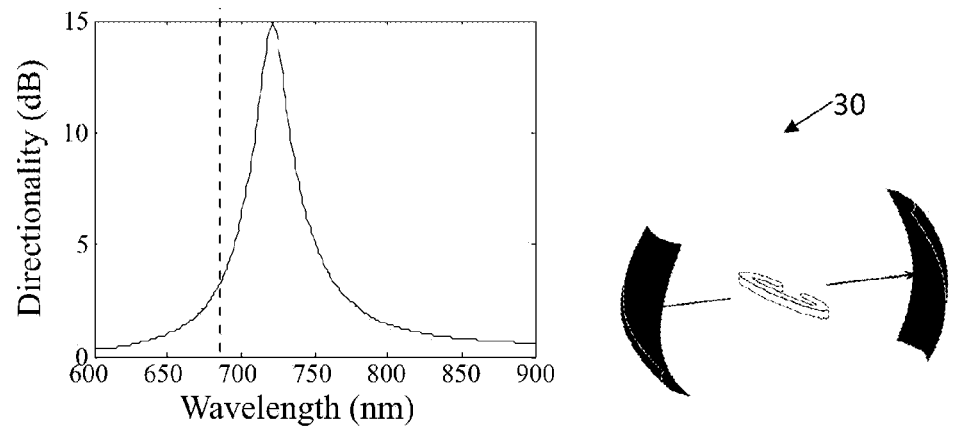
FIG. 5 shows the directionality in logarithmic scale for a single split ring resonator, as known in the art, and illustrates the spatial regions which are used to collect the right and left scattered radiation on which this directionality measure is based.

FIG. 5 shows the directionality along the x-axis on a dB-scale, being 10 log(r), where r is the ratio of the scattered radiation transmitted through a spatial region on the left of the x-axis and the scattered radiation transmitted through a spatial region on the right of the x-axis, as shown in the illustration 30 in FIG. 5. The directionality reaches a maximum of 15 dB at 720 nm for this specific example.

Figure 6:
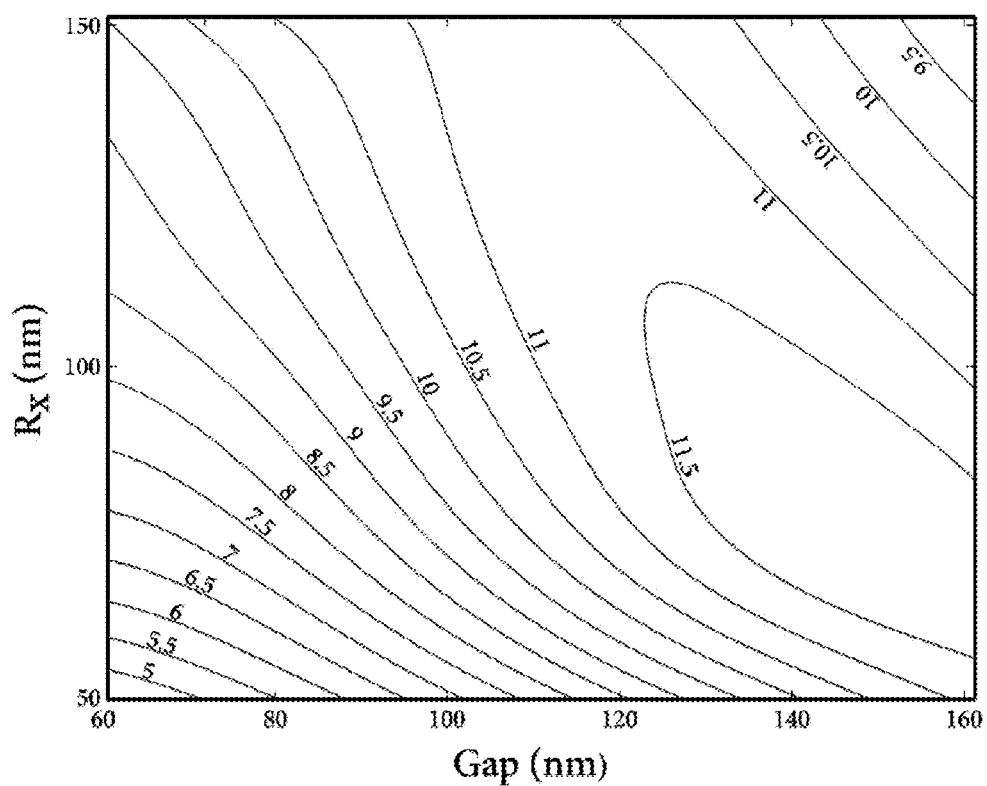
FIG. 6 show the maximal directionality reached in logarithmic scale as function of the radius $R_x$ and the gap width, G, for a single split ring resonator known in the art with a 200 nm y-radius $R_y$.

In order to reach good directivity, both the ellipticity of the ring and the gap width may be tuned. FIG. 6 shows the maximum of directivity for a single split ring resonator for a constant $R_y$ as function of $R_x$ and G. The most directional ring is a ring with a small $R_x$ and a large gap. If the gap is reduced, $R_x$ needs to increase in order to reach optimal directivity.

In the plasmonic structure 10 according to embodiments of the present disclosure shown in FIG. 1, the first part 13 and the second part 14 are furthermore functionally connected in a linkage region 15. In this linkage region, the electro conductor 12 is shaped such as to form a capacitive gap 16. For example, the first part 13 and the second part 14 may each form an open loop, with the ends of this loop separated by a gap. The ends of the loop of the first part 13 and of the loop of the second part 14 may furthermore be connected one on one in the linkage region 15, such that the gap separating the ends of each loop is shared, being the capacitive gap 16. Advantageously, the gap is kept as small as possible in order to really have a high field, so that there is a strong interaction with the medium or a fluorophore therein. However, as can be derived from FIG. 6, a trade off between optimal high field and directivity is to be made. Furthermore, the gap advantageously should be small enough so the structure can be treated as the combination of 2 C's. The resonance wavelengths can e.g. be tuned to the intended spectral domain by tuning particular dimensions of the structure, e.g. by tuning Rx and especially Ry.

Regarding the size of the antenna, it can actually be relatively large, for example up to Dy2=500 nm which is almost in the range of the wavelength. This is why using the dipole/dipole region is actually also interesting. In order to use the dipole-dipole region one needs to make the antenna small.

The electro conductor 12 is furthermore configured to direct the incident radiation of the first wavelength toward a first direction and to direct the incident radiation of the second wavelength toward a second direction, in which this first direction and this second direction are separated by an angle of at least 60°, for example, the first direction and the second direction may be substantially opposite spatial directions, e.g. may be opposite spatial directions.

Thus, the plasmonic structure 10 may be used as a plasmonic antenna that emits radiation to the right or left side of the antenna depending on the wavelength, e.g. as a plasmonic wavelength selective switch. The radiation incident on the plasmonic structure may for example be scattered radiation from a perpendicular beam or fluorescent radiation from a quantum emitter placed at the centre of the antenna. Apart from using this directionality to filter radiation or to send it out in a certain direction, measuring the degree of directionality by comparing the radiation collected at both sides of the antenna can advantageously also serve as a robust self-referenced measurement. Spectral information is immediately gained from the scattering pattern and can for example be used to detect a shift in refractive index of the medium surrounding the antenna in the case of scatted radiation, or to identify a fluorophore at the centre of the antenna.

Figure 7:
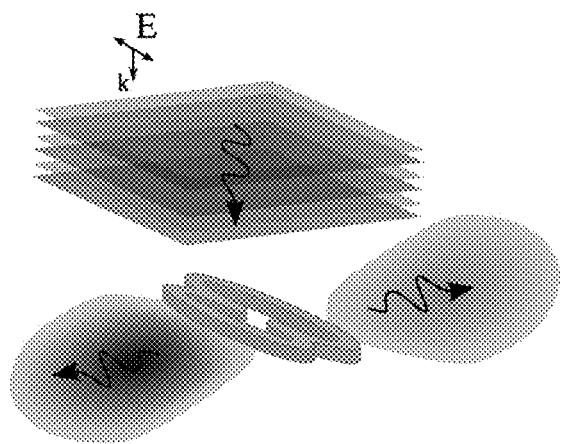
FIG. 7 shows a schematic representation of the directional scattering of a plasmonic structure according to embodiments of the present disclosure.

Having discussed the directionality in a single split ring resonator, e.g. the first part 13 or the second part 14 in isolation, two split ring resonators, e.g. with different $R_x$ and $R_y$, may be joined at the gap in embodiments according to the present disclosure. This type of resonator may scatter directionally to the left at one wavelength and scatter to the right at another. The resonators shape and the intended effect can be seen in FIG. 7, showing a planar electromagnetic wave E with wave vector k which comprises components of the first and second wavelength that impinges onto the plasmonic structure according to embodiments and is split into two outgoing waves as function of the wavelength in two opposing directions.

Figure 8:
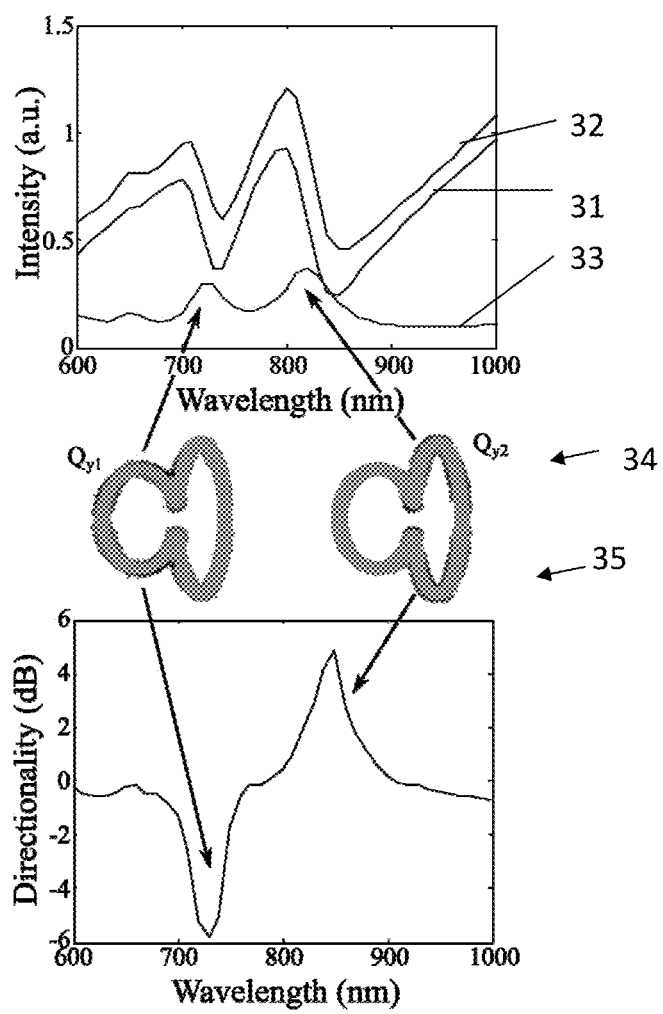
FIG. 8 shows extinction, scattering and absorption spectra of a plasmonic structure according to embodiments of the present disclosure, a charge plot of the plasmonic structure at the two resonances and the obtained directionality of the plasmonic structure.

FIG. 8 shows the spectrum of this type of resonator. Two clear resonances, $Q_{y1}$ and $Q_{y2}$, can be seen in the absorption spectrum 33 at 715 nm and 810 nm, respectively. The scattering 31 and extinction 32 spectrums show the clear asymmetry associated with Fano resonances. These resonances can be linked to the left and right parts of the antenna. The charge plot 34 in FIG. 8 illustrates this. At the red side of both resonances directionality can be observed, as illustrated in the bottom plot 35 in FIG. 8. The resonance at 715 nm, associated with the left part of the resonator, shows directionality to the right while the resonance at 810 nm, associated with the right part of the resonator, shows directionality to the left.

Figure 10:
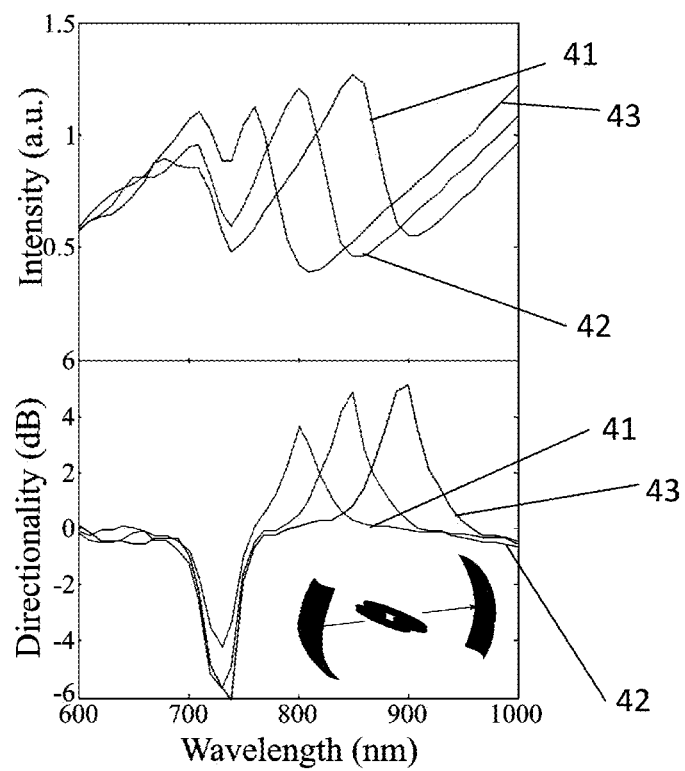
FIG. 10 shows different extinction spectra and corresponding directionality of plasmonic structures according to embodiments with a $R_{y1}$ of 250 nm and a $R_{y2}$ of 275 nm, 300 nm and 325 nm.

It is to be noted that this is opposite to what is seen in the single split ring resonator. A single split ring resonator with a gap on the right side scatters to the left. Yet the resonance at 715 nm scatters to the right. The combination with another split ring resonator may cause a change in the phase of the resonances that builds up the scatter pattern, see FIG. 4. However, the red spectrum side of the resonances stays a region with a low net dipole moment. Thus, by tuning $R_x$ and G, directionality can still be reached, albeit in the other direction. By tuning $R_{y1}$ and $R_{y2}$ the spectral position of the resonances can be changed. Increasing $R_y$ red shifts the resonance. By decreasing the difference between $R_{y1}$ and $R_{y2}$, the resonances can thus be pushed closer together. The spectra and the directionality for a double C resonator with different $R_{y2}$ can be seen in FIG. 10. When the resonances are very close together the directionality starts to decrease. In FIG. 10, different extinction spectra and corresponding directionality of double split ring resonators according to embodiments are shown with a $R_{y1}$ of 250 nm and a $R_{y2}$ of 275 nm in plot 41, of 300 nm in plot 42 and 325 nm in plot 43.

Figure 11:
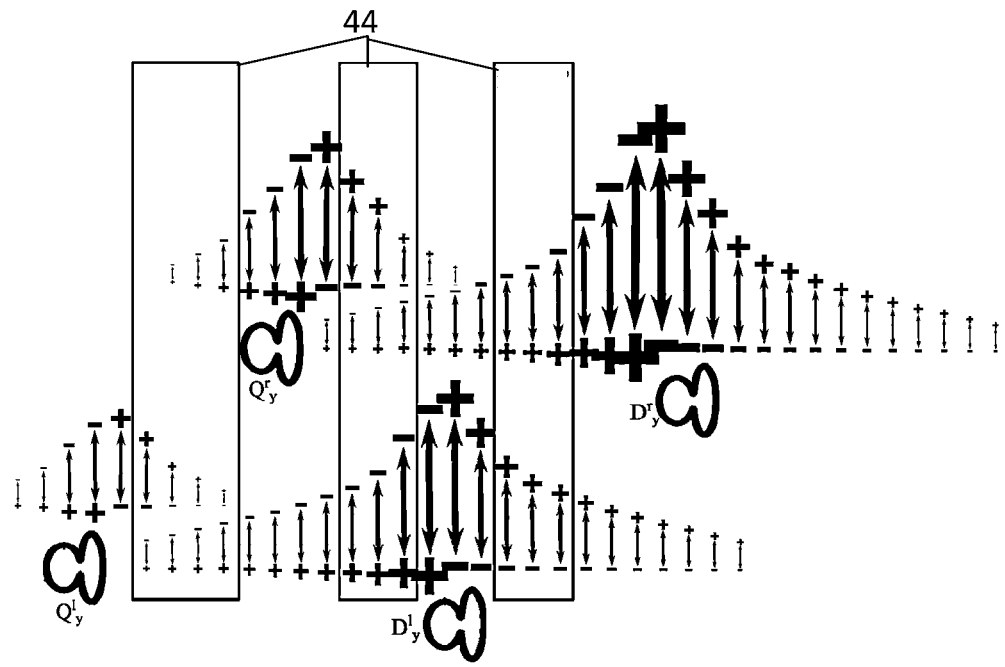
FIG. 11 shows the net dipole contribution associated with the different resonances present in a plasmonic structure according to embodiments.
Figure 12:
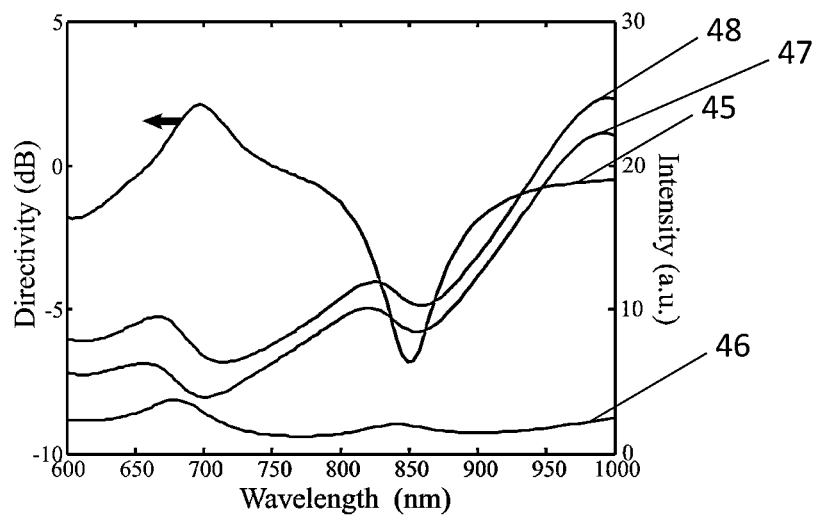
FIG. 12 shows the directivity and radiative, absorption and extinction spectra of a plasmonic structure according to embodiments configured as a double C-antenna on glass.
Figure 13:
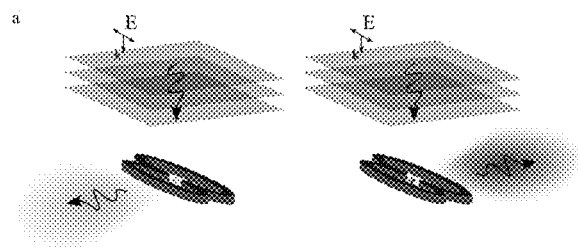
FIG. 13 shows a schematic representation of the directional emission at two different wavelengths for plasmonic structure according to embodiments having a fluorophore quantum emitter arranged in or near the gap.

In addition to the two regions with a low net dipole that are present also in the single split ring resonator, the double split ring resonator has also a low net dipole between the two dipole resonances of the left and right split ring resonator. The three low net dipole regions 44 where directional scattering might occur are schematically indicated in FIG. 11. The dipole-dipole-region can also be used to tune the scatter directionally. To make this region accessible for visible wavelengths, the resonator can be scaled down. Advantages of using this region instead of the lower region are that it is easier to obtain good directionality when the antenna lies on a substrate and that it suffers much less from scattering in the Y-direction. FIG. 12 shows the radiative 47, absorption 46 and extinction 48 spectra and the directivity 45 for a gold double split ring resonator antenna on a glass substrate tuned for optimal directionality. In the plasmonic structure 10 according to embodiments of the present disclosure, the first part 13 and the second part 14 are furthermore functionally connected in a linkage region 15, where the electro conductor 12 is shaped such as to form a capacitive gap 16. From the charge plot 34 in FIG. 8, it can be seen that for both resonances charge accumulates at the gap 16, causing a high electric field in this central region. A fluorophore placed in or near the gap 16 may advantageously excite both the left or right part of the resonator, depending on its emission wavelength. This effect is schematically illustrated in FIG. 13, in which short wavelength incoming radiation E with wave vector k excites the quantum emitter, and is directed to either direction depending on the fluorophore emission wavelength.

Figure 14:
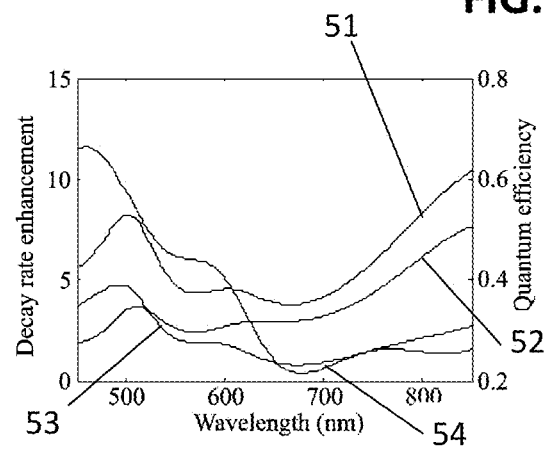
FIG. 14 shows total, non-radiative and radiative decay rate enhancement compared to the decay in free space for the plasmonic structure according to embodiments having a quantum emitter arranged in or near the gap.

FIG. 14 shows the total 51, non-radiative 52 and radiative 53 enhancement of the decay rate of a quantum emitter in or near the gap 16 of a plasmonic structure according to embodiments. The ratio 54 of the radiative and total decay rate is the quantum efficiency and is mapped on the right axis. It is to be noted that the resonances of the plasmonic structure having a quantum emitter in or near the gap lie at a lower wavelength than for the plasmonic structure without quantum emitter discussed hereinabove. The simulation results depicted here were performed with an aluminium antenna instead of a gold one. This material change causes a blue shift making the resonances accessible for wider range of fluorophores.

Figure 15:
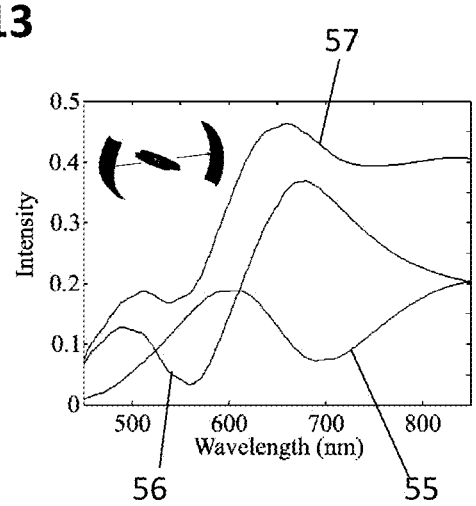
FIG. 15 shows the portion of the radiative decay rate associated with emission to the right, to the left and the sum of both for the plasmonic structure according to embodiments having a quantum emitter arranged in or near the gap.
Figure 16:
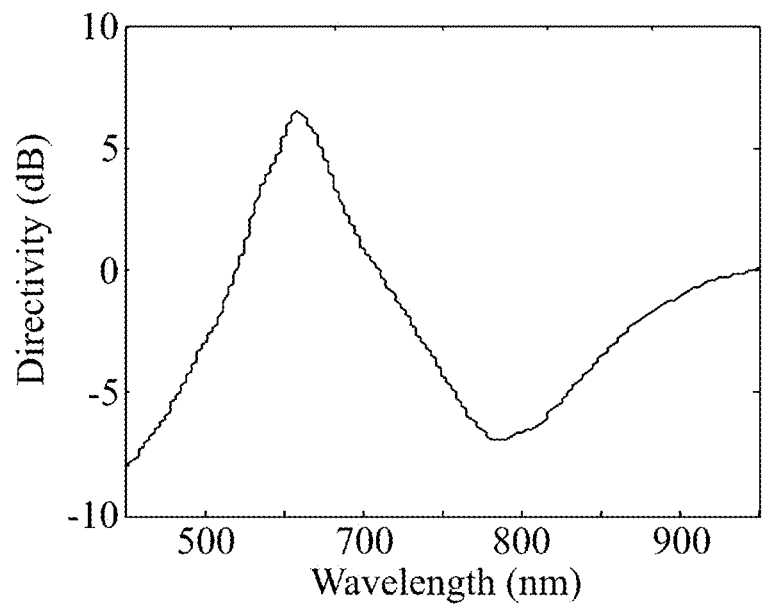
FIG. 16 shows the directivity in dB for the plasmonic structure according to embodiments having a quantum emitter arranged in or near the gap.

FIG. 15 shows the contribution of the radiative decay rate that scattered to the left or to the right. At 570 nm, the fluorophore excites the left part of the plasmonic structure and most of the radiation scatters to the right side 56. At 690 m, the right part is excited and radiation scatters to the left 55. The sum of both left scattered radiation 55 and right scattered radiation 56 is also shown in plot 57. The ratio of the left and right scattered radiation on a dB-scale is shown in FIG. 16. Both resonances peak at about ±6 dB.

This changing emission pattern can be used to identify the quantum emitter at the centre. Depending on the wavelength of the emitted radiation by the quantum emitter the antenna will emit the radiation in a certain left to right ratio. Since different fluorophores emit at a different wavelength, a quantum emitter can be identified by the left-right ratio.

In embodiments according to the present disclosure, the capacitive gap 16 may therefore comprise a quantum emitter. Alternatively, the capacitive gap 16 may be functionalized to capture a quantum emitter, e.g. to capture at least one of a plurality of quantum emitter, e.g. fluorescently labelled bio-particles.

Figure 17:
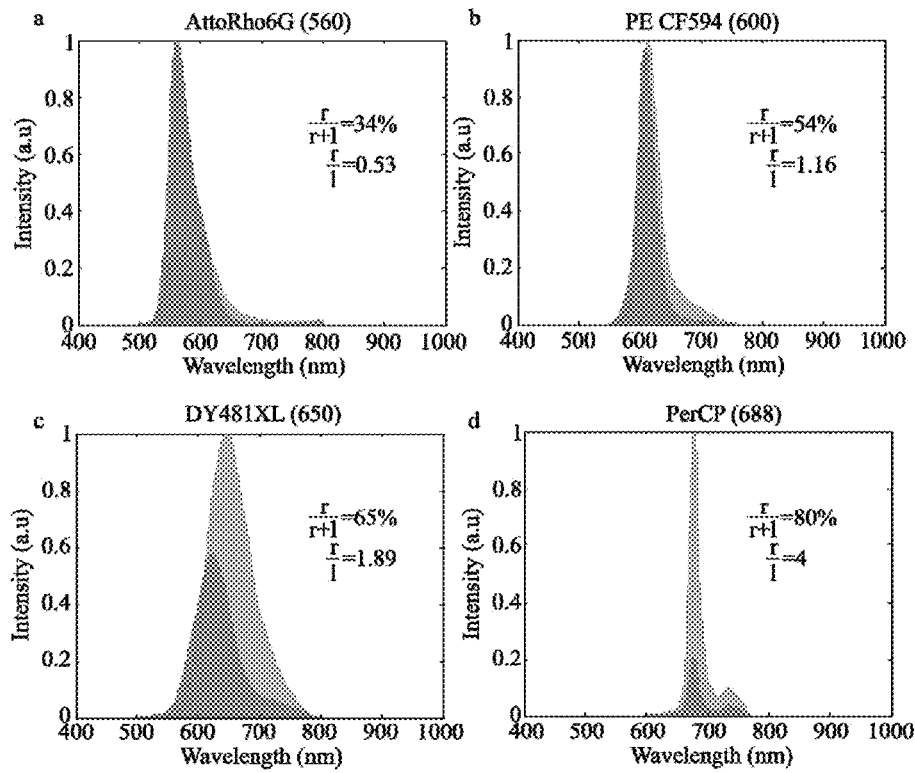
FIG. 17 shows the radiation intensity emitted to the right and left in function of the wavelength for 4 different dyes placed in the central gap of a plasmonic structure according to embodiments.
Figure 18:
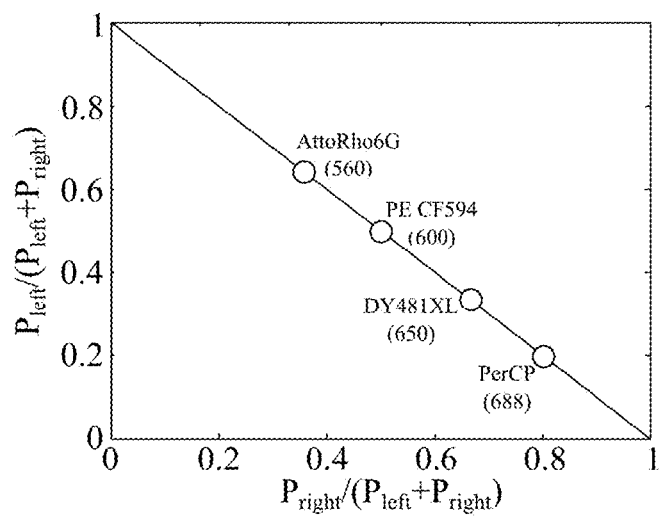
FIG. 18 shows the left-right power fraction for the four different dyes placed in the central gap of a plasmonic structure according to embodiments.

However, the fluorophores do not emit in a single wavelength. They have a certain bandwidth. Because of this the total emitted radiation scattered to the left or the right is spread out. In FIG. 17, the emitted radiation to the left and right side for four different dyes, AttoRho6G, PECF594, DY481XL and PerCP, is shown as function of the wavelength. The left and right scattered radiation was integrated and compared. In the case of the AttoRho6G dye, which emits around 560 nm, almost double the amount of power is sent to the left compared to the right, while for PerCP four times as much is send to the right compared to the left. In FIG. 18, the fractions of left and right emitted radiation are shown. Every dye takes a specific place on the curve.

Figure 19:
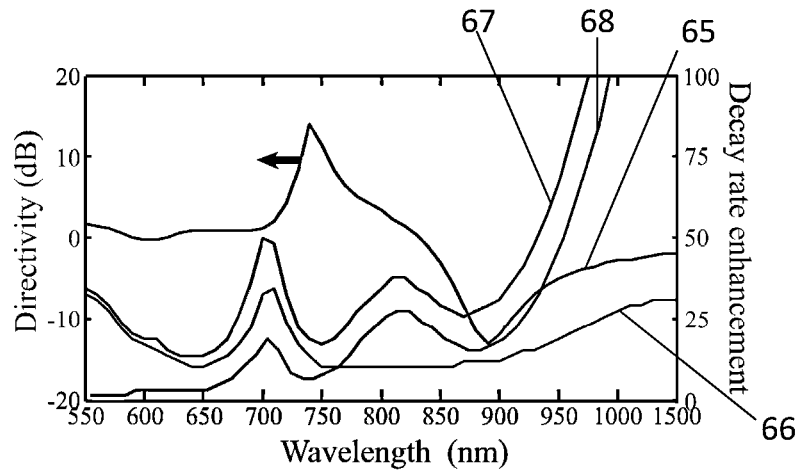
FIG. 19 shows the directivity (units on right axis), and radiative, non-radiative and total enhancement of the emission (units on left axis) from a dye in the gap of a golden double C-shaped antenna on glass according to embodiments of the present disclosure.

Just as discussed for directional scattering without quantum emitter interaction in the plasmonic structure's gap, the dipole-dipole region can also be used to cause directional emission. As discussed hereinabove, it may be easier to obtain directional scattering for an antenna on glass. FIG. 19 shows the directivity 65 for a gold antenna on a glass substrate using this region, as well as radiative 68, non-radiative 66 and total enhancement 67 of the emission from a quantum emitter in the gap of the plasmonic structure. Directivity larger than 12 dB is reached in both directions.

Figure 20:
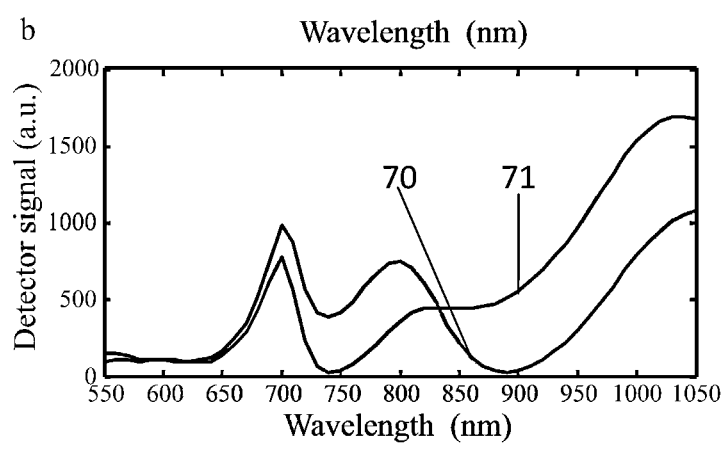
FIG. 20 shows the intensity captured by detectors positioned right and left of the emission from a quantum emitter in the gap of a golden double C-shaped antenna on glass according to embodiments of the present disclosure.

FIG. 20 shows a plot of the intensity as captured by a detector positioned on the right 71 and on the left side 70.

Figure 9:
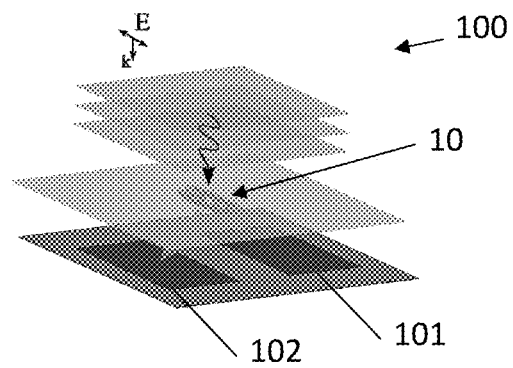
FIG. 9 shows an example compact sensor using a plasmonic structure according to embodiments of the present disclosure.

In a second aspect, the present disclosure relates to a sensor comprising a plasmonic structure 10 according to embodiments of the first aspect of the present disclosure. FIG. 9 shows an example compact sensor 100 according to embodiments of this second aspect of the present disclosure. This sensor further comprises a first radiation detection element 101 and a second radiation detection element 102. The plasmonic structure 10 is arranged such as to direct radiation E incident on the plasmonic structure of the first wavelength predominantly toward the first radiation detection element 101, and to direct radiation incident on the plasmonic structure of the second wavelength predominantly toward the second radiation detection element 102. The sensor may comprise a sample positioning means for bringing a sample into contact with the plasmonic structure. The sample positioning means may comprise a detection surface. Such a surface may be functionalised for capturing targets of interest. Functionalised surfaces are well known by the skilled person.

In embodiments where fluorescence is used, the sensor may be adapted for guiding an excitation beam towards the plasmonic structure. The sensor also may comprise an excitation source for generating an excitation beam. Furthermore optical components and/or waveguides may be incorporated for guiding radiation to the structure. In some embodiments waveguides used for directing the fluorescence radiation towards the detection elements may also be used for directing the excitation radiation towards the plasmonic structure. The sensor may, amongst others in such cases, comprise a filter covering the first radiation detection element 101 and the second radiation detection element 102 for filtering out the portion of a excitation radiation.

The sensor also may comprise a processor for processing radiation sensed at the first and/or second radiation detection element and/or for determining a ratio of the amount of radiation detected in the first radiation detection element and the amount of radiation detected in the second radiation detection element. Such a processor furthermore may be programmed for deriving therefrom a property of the sample under study.

In one embodiment, the plasmonic structure, e.g. a double split ring antenna as described hereinabove, is arranged close to two detection regions, e.g. two detection elements for measuring the radiation. Furthermore, the sensor may comprise a filter covering the detection regions, which is adapted for filtering out the portion of an excitation beam incident the plasmonic structure that is transmitted through the plasmonic structure substantially unaffected. Thus, substantially only the high angle side scattering of the plasmonic structure may be detected by the detection regions. Furthermore, when the refractive index of the medium changes due to analytes binding to the plasmonic structure, for example the resonance frequency can shift and a change in the left-right scattering ratio can be detected.

Figure 21:
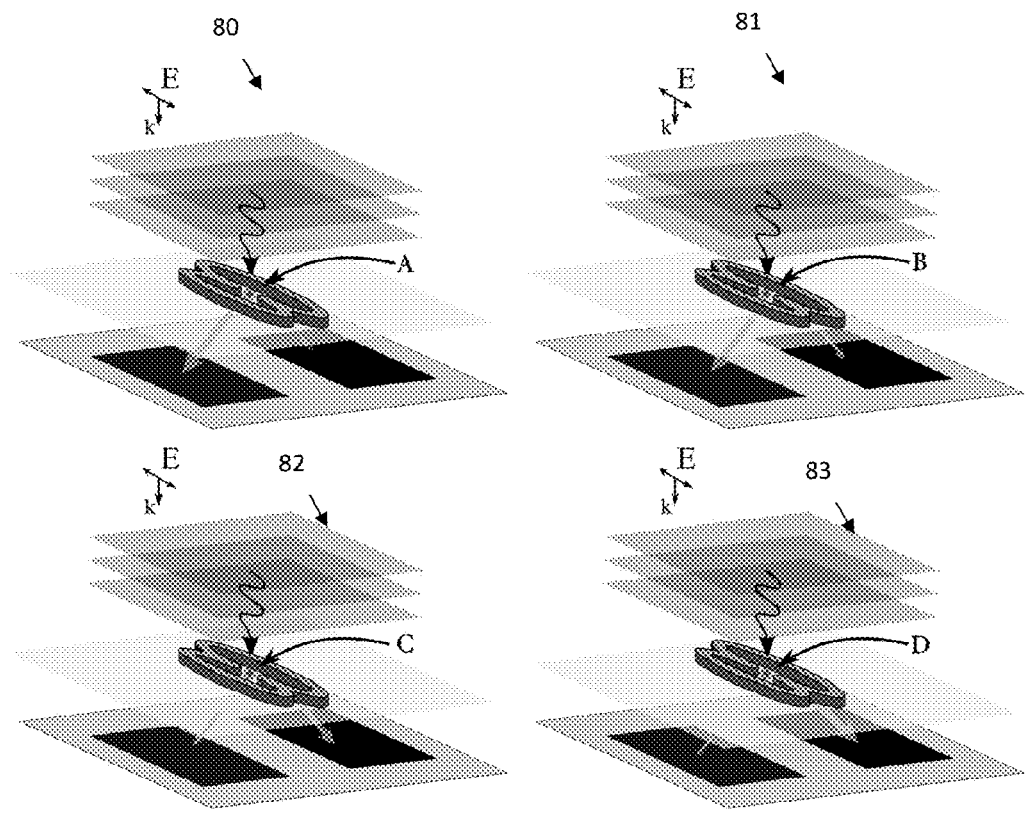
FIG. 21 shows a compact sensor according to embodiments of the present disclosure, where the left-right scatter ratio are used to identify the quantum emitter located in the gap of the plasmonic structure.

When a quantum emitter binds in the gap 16 it can be easily identified by the intensity ratio of the intensities measured by these detectors. This is illustrated in FIG. 21. The darker regions represent the two detection regions and are shielded from the excitation beam by a filter. Almost all the radiation of a quantum emitter A is sent to the left detector, as shown in illustration 80, most of the radiation of a quantum emitter B is sent to the left detector, as shown in illustration 81, most of the radiation of an quantum emitter C is sent to the right detector, as shown in illustration 82, and almost all of the radiation of a quantum emitter D is sent to the right detector, as shown in illustration 83.

Figure 22:
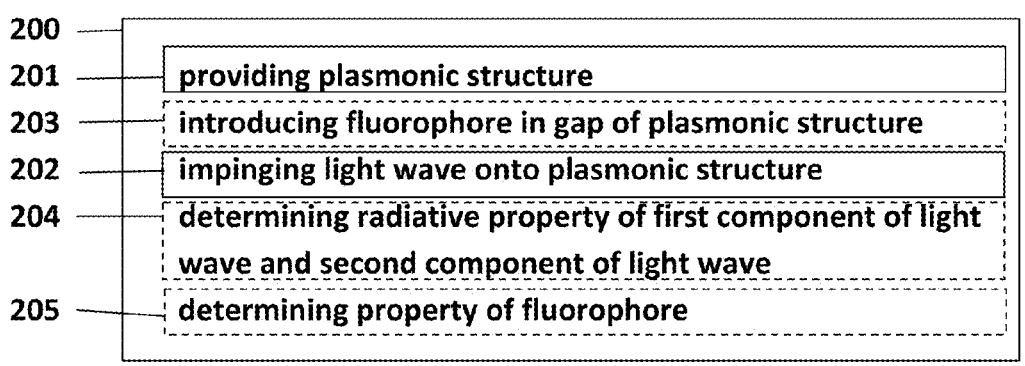
FIG. 22 shows an example method according to embodiments of the present disclosure.
Figure 23:
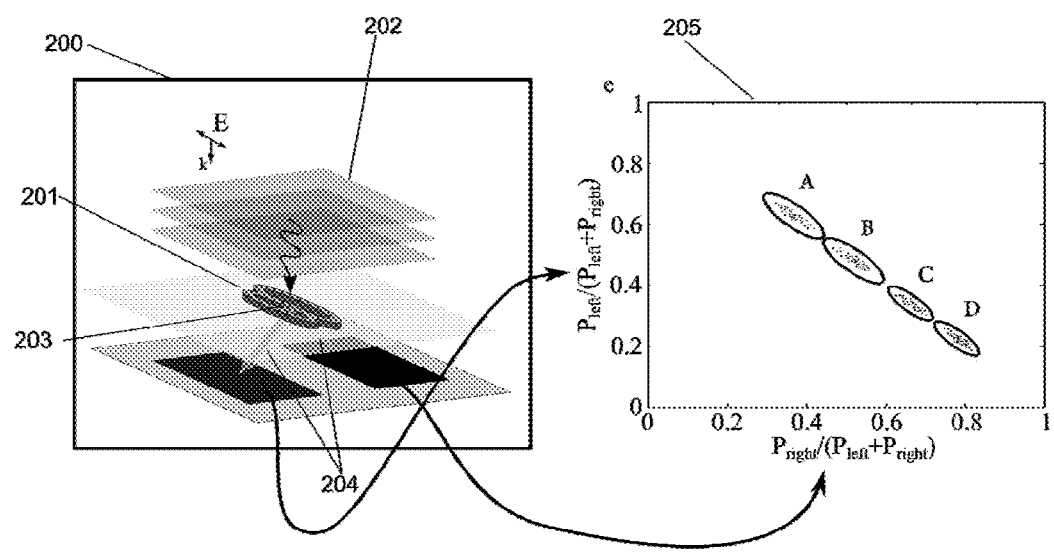
FIG. 23 shows the elements of a system and the corresponding method steps where the elements play an important role, according to an embodiment of the present disclosure.

In a third aspect, the present disclosure relates to a method for wavelength selective switching of radiation. An example method 200 according to embodiments of this third aspect of the disclosure is shown in FIG. 22. The elements introduced during the corresponding method steps are shown in FIG. 23, whereby for each element, the corresponding method step is indicated. The method 200 comprises providing 201 a plasmonic structure 10 comprising an electro conductor 12 which comprises a first part 13 configured to provide a first series of plasmon resonance modes for incident radiation (which result in directive radiation for a first wavelength) and a second part 14 configured to provide a second series of plasmon resonance modes for incident radiation (which result in directive radiation for a second wavelength), the first part 13 and second part 14 being functionally connected in a linkage region 15. The electro conductor 12 is furthermore configured to direct radiation incident on the plasmonic structure of a first wavelength predominantly toward a first direction and to direct radiation incident on the plasmonic structure of a second wavelength predominantly toward a second direction. Particularly, providing 201 the plasmonic structure 10 may comprise providing a plasmonic structure 10 according to the first aspect of the present disclosure.

The method 200 may also comprise introducing 203 a fluorophore in or near a capacitive gap 16 formed in the linkage region 15. In one embodiment, the method comprises providing a sample with differently fluorescently labelled targets of interest. The fluorescent labels may be selected so that these emit at different wavelengths, the radiation being directed to different directions or in different proportions to different directions. The method thus may allow identifying different targets. The method may comprise exciting fluorophores by directing an excitation beam to the plasmonic structure. Alternatively, the method also can be used for identifying a change in a property of the material near the plasmonic structure, e.g. for identifying a refractive index change near the plasmonic structure. The refractive index change may be induced by binding of targets on a sensor surface at or near the plasmonic structure. In order to identify targets of interest in a sample, the surface of the plasmonic structure may be functionalised for receiving the targets of interest. Functionalising a surface is a technique well known by the person skilled in the art and therefore is not further discussed here in detail.

The method 200 further comprises impinging 202 a radiation wave onto the plasmonic structure such as to direct a first component of the radiation wave corresponding to the first wavelength toward the first direction and to direct a second component of the radiation wave corresponding to the second wavelength toward the second direction.

The method 200 may also comprise determining 204 a radiative property, e.g. a radiation intensity, of the first component of the radiation wave and of the second component of the radiation wave.

The method 200 may also comprise determining 205 a property of the fluorophore, for example identifying the fluorophore from a plurality of possible fluorophores, taking into account the determined radiative property of the first component and the second component.

The invention claimed is:

1. A plasmonic structure comprising:
   a substrate; and
   at least one electro conductor provided in or on the substrate, wherein the at least one electro conductor includes a first part configured to provide a first series of plasmon resonance modes for incident radiation of a first wavelength, and a second part configured to provide a second series of plasmon resonance modes for incident radiation of a second wavelength, wherein the first part and second part being functionally connected in a linkage region,
   wherein the electro conductor being shaped in the linkage region such as to form a capacitive gap,
   wherein the electro conductor is further configured to direct radiation incident on the plasmonic structure of the first wavelength predominantly toward a first direction and to direct radiation incident on the plasmonic structure of the second wavelength predominantly toward a second direction, and wherein the first direction and the second direction being separated by an angle of at least 60°.

2. The plasmonic structure according to claim 1, wherein the first direction and the second direction are substantially opposite spatial directions.

3. The plasmonic structure according to claim 2, wherein the first part forms a first plasmonic split ring resonator and the second part forms a second plasmonic split ring resonator.

4. The plasmonic structure according to claim 3, wherein the first plasmonic split ring resonator and the second plasmonic split ring resonator each have an elliptical shape.

5. The plasmonic structure according to claim 1, wherein the substrate comprises glass.

6. The plasmonic structure according to claim 1, wherein the substrate forms part of a waveguide in an integrated photonics system.

7. The plasmonic structure according to claim 1, wherein the capacitive gap comprises a quantum emitter or in which the capacitive gap is functionalized to capture a quantum emitter.

8. A sensor comprising:
   a plasmonic structure according to claim 1;
   a first radiation detection element; and
   a second radiation detection element,
   wherein the plasmonic structure being arranged such as to direct radiation incident on the plasmonic structure of the first wavelength predominantly toward the first radiation detection element, and to direct radiation incident on the plasmonic structure of the second wavelength predominantly toward the second radiation detection element.

9. The sensor according to claim 8, further comprising a filter covering the first radiation detection element and the second radiation detection element, wherein the filter being adapted for filtering out the portion of a radiation wave incident on the plasmonic structure that is transmitted through the plasmonic structure substantially unaffected.

10. The sensor according to claim 9, wherein the sensor further comprises a sample positioning means for bringing a sample into contact with the plasmonic structure.

11. The sensor according to claim 10, wherein the sensor further comprises an excitation source for exciting fluorescent labels being positioned near the plasmonic structure, and the sensor further being adapted for characterizing differently fluorescent labeled targets of interest in the sample.

12. The sensor according to claim 11, wherein the sensor further comprises a processor for processing radiation sensed at the first and/or second radiation detection element and/or for determining a ratio of the amount of radiation detected in the first radiation detection element and the amount of radiation detected in the second radiation detection element.

13. A method for wavelength selective switching of radiation, the method comprising:
   providing a plasmonic structure comprising an electro conductor that includes a first part configured to provide a first plasmon resonance mode for incident radiation of a first wavelength and a second part configured to provide a second plasmon resonance mode for incident radiation of a second wavelength, wherein the first part and second part being functionally connected in a linkage region, wherein the electro conductor is further configured to direct radiation incident on the plasmonic structure of the first wavelength predominantly toward a first direction and to direct radiation incident on the plasmonic structure of the second wavelength predominantly toward a second direction; and impinging a radiation wave onto the plasmonic structure such as to direct a first component of the radiation wave corresponding to the first wavelength toward the first direction and to direct a second component of the radiation wave corresponding to the second wavelength toward the second direction.

14. The method according to claim 13, further comprising:

introducing a fluorophore in or near a capacitive gap formed in the linkage region;

determining a radiative property of the first component of the radiation wave and of the second component of the radiation wave; and determining a property of the fluorophore taking into account the determined radiative property of the first component and the second component.

15. The method according to claim 14, the method further comprising evaluating a ratio of the radiation directed to the first direction and the radiation directed to the second direction.

* * * * *